(12) United States Patent
Schelin et al.

(10) Patent No.: US 11,938,289 B2
(45) Date of Patent: Mar. 26, 2024

(54) KIT AND METHOD INTENDED FOR PROSTATE SURGERY

(71) Applicant: ProstaLund AB, Lund (SE)

(72) Inventors: Sonny Schelin, Rockneby (SE); Anette Israelsson, Lund (SE); Johan Wennerholm, Lomma (SE); Thomas Falk, Staffanstorp (SE)

(73) Assignee: PROSTALUND AB, Lund (SE)

( * ) Notice: Subject to any disclaimer, the term of this patent is extended or adjusted under 35 U.S.C. 154(b) by 542 days.

(21) Appl. No.: 17/160,728

(22) Filed: Jan. 28, 2021

(65) Prior Publication Data

US 2022/0233830 A1  Jul. 28, 2022

(51) Int. Cl.
| | |
|---|---|
| *A61M 25/10* | (2013.01) |
| *A61M 5/158* | (2006.01) |
| *A61M 25/00* | (2006.01) |
| *A61M 25/04* | (2006.01) |
| *A61M 27/00* | (2006.01) |

(52) U.S. Cl.
CPC .. *A61M 25/10185* (2013.11); *A61M 25/0084* (2013.01); *A61M 2025/0085* (2013.01);
(Continued)

(58) Field of Classification Search
CPC ........ A61M 25/10185; A61M 25/0084; A61M 2025/0085; A61M 2025/105;
(Continued)

(56) References Cited

U.S. PATENT DOCUMENTS 3,977,408 A * 8/1976 MacKew ........ A61M 25/10181
604/102.03
5,843,016 A   12/1998 Lugnani et al.
(Continued)

FOREIGN PATENT DOCUMENTS

| WO | WO200149195 A1 | 7/2001 | |
|---|---|---|---|
| WO | WO-0198764 A2 | 12/2001 | |
| WO | WO-2005118799 A1 * | 12/2005 | ............... C07K 7/08 |

OTHER PUBLICATIONS

Swedish Search Report for Patent Application No. 2150095-4; dated Jan. 28, 2021, 2 pages.
(Continued)

*Primary Examiner* — Robert J Utama
*Assistant Examiner* — Hamza A Darb
(74) *Attorney, Agent, or Firm* — MOSER TABOADA

(57) ABSTRACT

The present invention describes a method for performing a prostate surgical treatment, said method comprising:
arranging a catheter 1 inside of a urethra of a patient and anchored against the bladder neck of the patient subsequent to the filling of the balloon stopper unit 5 with a fluid when the balloon stopper unit 5 is arranged inside of the bladder of a patient;
said method also comprising
injecting at least one anesthetic agent and adrenaline or injecting botulinum toxin (Botox) and/or penicillin to the prostate via the injection tube 9 and the hollow tip 10 at an intended position of the prostate.
Moreover, the present invention also refers to a kit comprising a catheter 1 according to the present invention and one or more syringe(s) 1000 containing adrenaline and at least one anesthetic agent and/or at least a syringe 1000 or vial containing botulinum toxin (Botox) and/or penicillin.

13 Claims, 2 Drawing Sheets

(52) U.S. Cl.
CPC . *A61M 2025/105* (2013.01); *A61M 2202/048* (2013.01); *A61M 2202/07* (2013.01); *A61M 2202/203* (2013.01); *A61M 2210/1096* (2013.01); *A61M 2210/166* (2013.01)

(58) Field of Classification Search
CPC ........ A61M 2202/048; A61M 2202/07; A61M 2202/203; A61M 2210/1096; A61M 2210/166; A61M 2025/0096; A61M 5/158; A61M 25/0017; A61M 25/04; A61M 25/10; A61M 27/00; A61M 2025/0092; A61B 2018/00982
See application file for complete search history.

(56) References Cited

U.S. PATENT DOCUMENTS

| | | |
|---|---|---|
| 6,477,426 B1 | 11/2002 | Fenn et al. |
| 6,524,270 B1 | 2/2003 | Bolmsjö et al. |
| 2002/0082610 A1* | 6/2002 | Cioanta ................. A61B 18/04 623/1.11 |
| 2005/0124852 A1* | 6/2005 | Bolmsjo .......... A61B 17/12186 600/29 |
| 2008/0172041 A1* | 7/2008 | Shehata ................ A61M 25/04 604/544 |
| 2010/0198139 A1 | 8/2010 | Glickman |
| 2011/0046600 A1* | 2/2011 | Crank ............... A61M 25/0068 604/500 |
| 2014/0276663 A1* | 9/2014 | Pinchuk .......... A61M 25/10185 604/544 |
| 2019/0076188 A1 | 3/2019 | Fischell et al. |
| 2020/0345976 A1* | 11/2020 | Kalt ..................... A61M 25/10 |

OTHER PUBLICATIONS

International Search Report and Written Opinion for Application No. PCT/SE2022/050080, dated Mar. 1, 2022, 7 pages.

* cited by examiner

KIT AND METHOD INTENDED FOR PROSTATE SURGERY

FIELD OF THE INVENTION

The present invention relates to a kit and method intended for prostate surgery or treatment.

TECHNICAL BACKGROUND

There are several known catheters suitable for prostate surgery and treatments. For instance, in WO01/49195 there is disclosed a device for treatment of the prostate, comprising a catheter for treatment which is inserted through the urethra, wherein the catheter is provided with a front portion that comprises an expandable container for positioning of the catheter with said front portion in the urinary bladder, wherein at least one hollow tip is provided to be extended from the catheter into the prostate tissue surrounding catheter and wherein the tip is connected with a syringe for supply of an astringent and analgesic medicine.

The present invention provides an improved kit intended for prostate surgery and prostate treatment. Furthermore, the present invention is also directed to providing a novel and improved method in which said kit is used. Both these and several additional embodiments are disclosed and further explained below.

SUMMARY OF THE INVENTION

The present invention refers to a kit comprising
a catheter comprising
   an introduction unit with a top, said introduction unit also comprising a drainage lumen hole for drainage of a urinary bladder;
   a balloon stopper unit in connection with and thus possible to fill via a balloon inflation connection and balloon filling tube arranged inside of the introduction unit, wherein filling of the balloon stopper unit with a fluid is intended when the balloon stopper unit is arranged inside of the bladder of a patient to provide for a stopper function of the balloon stopper unit against the bladder neck of the patient;
said catheter also comprising
   an injection connection connected to an injection tube arranged inside of the introduction unit, which injection tube extends in a hollow tip arranged to be provided to extend from the introduction unit;
   a drainage outlet;
said kit also comprising
   at least one or more syringe(s) connectable to the injection connection of the catheter and containing adrenaline and at least one anesthetic agent, and/or
   at least a syringe or vial containing botulinum toxin (Botox) and/or penicillin.

The present invention differs in relation to device disclosed in WO01/49195 in relation to improvements of the catheter as such and the kit provided according to the present invention. Furthermore, the method according to the present invention is further disclosed below and differs from the suggested handling of the catheter according to WO01/49195 in several ways. As an example, the method according to the present invention provides an improved method for suppressing both blood flow to the prostate, which is of interest to eliminate or at least diminish cooling down of the prostate during e.g. a heat treatment thereof, and also blood supply to the prostate, which in turn is of interest to minimize the blood coming out at the surface of the prostate during a trimming action in a transurethral resection of the prostate (TURP) surgery.

Such differences and further embodiments according to the present invention will become clear from reviewing the full description below.

Specific Embodiments

Below several embodiments of the present invention are provided and explained further.

According to one embodiment of the present invention, a multi-connection unit is arranged at an end of the catheter, said end being opposite to the top of the introduction unit, said multi-connection unit being arranged to hold the balloon inflation connection, the injection connection and at least a first portion of the drainage outlet. One embodiment of such a multi-connection unit is shown in the attached figures. Furthermore, a multi-connection as provided according to the present invention has the advantage of providing a simple and user-friendly arrangement which may hold all units of the catheter in place. This also simplifies when connecting a syringe according to the present invention to the catheter.

Moreover, according to yet another embodiment of the present invention, one or more of the balloon inflation connection, the injection connection and the drainage outlet are arranged with one or more valve(s). One such alternative is shown for the balloon inflation connection in FIG. 2.

Furthermore, according to yet another embodiment of the present invention, the hollow tip arranged to be provided to extend from the introduction unit has a length in the range of 30-60 mm, preferably 40-50 mm, extending from the introduction unit. This length is suitable when introducing the hollow tip into the prostate.

In relation to the above it should be mentioned that the injection tube and hollow tip may be provided as one single unit, thus the hollow tip is the final part of the injection tube which is possible to extend from the introduction unit and thus possible to introduce into the prostate. Furthermore, according to one embodiment of the present invention the hollow tip arranged to be provided to extend from the introduction unit is arranged to extend from the introduction unit with an angle in the range of 20-40° from the introduction unit. This angle is suitable angle for introducing the hollow tip into the prostate.

Moreover, according to yet another embodiment of the present invention, the injection tube and hollow tip are made of PEEK (polyether ether ketone). Again, suitably the injection tube and hollow tip are provided as one single unit, and where the hollow tip is only the final part of that single unit. Furthermore, in relation to material choices, another aspect of the present invention may be discussed further. To be able to locate the position of the hollow tip may be important when performing a prostate surgery method, such as a method according to the present invention described below. As the catheter is arranged inside of the urethra when the hollow tip is about to be introduced into the prostate, to enable this is not an obvious task. A material possible to see when using assisting technologies, such as ultrasound, CT etc., during surgery may be of interest according to the present invention. At the same time, the material of the hollow tip and injection tube may be suitable for introducing into the prostate. PEEK is one such suitable material. Furthermore, the injection tube may be reinforced, such as by use of a steel material. Moreover, the locating of the hollow tip may be enabled by other means, such as e.g. by the use of nanoparticles.

According to one embodiment of the present invention, the injection tube has a stopper so that the injection tube cannot be pulled out from the introduction unit entirely, preferably wherein the injection tube has a stopper and wherein there is a distance marking provided outside of the injection tube. These features simplify the using as well as helps a user to calculate the position of the injection tube and hollos tip. This simplifies for the user to ensure that the hollow tip is introduced into the prostate at the intended place.

Moreover, according to yet another embodiment, the introduction unit is made of a rubber or plastic material, preferably wherein the introduction unit is provided with a marking in its lower portion. Such a type of material, neither too stiff not too flexible, e.g. made of a silicone material, ensures that the user can understand the position of the catheter inside of the urethra and also eliminates the risk of the catheter being twisted inside of the urethra. Therefore, this marking may be said to show if the catheter is held in place inside of the urethra and not twisted. Moreover, and as mentioned, the distance marking of the injection tube provides assistance for the user to know the position of the injection tube and thus hollow tip before introducing the same into the prostate.

In relation to the above it may be mentioned that a lubricant, such as vaseline, may be used to ensure that the catheter is simple to insert into the urethra and simple to pull back and forth inside of the urethra, both to find the right position and also as part of the method according to the present invention, which is further explained below. Also the use of a lubricant may be seen as means to increase the correct locating of the catheter and hollow tip before inserting/introducing the hollow tip into the prostate. Based on the above, according to one embodiment of the present invention, the kit also comprises a lubricant, such as vaseline. Furthermore, it should be noted that at least the introduction unit of the catheter according to the present invention may also be produced in or coated by a sliding material so that the catheter is simple to insert into the urethra.

The present invention also refers to a method for performing a prostate surgical treatment, said method comprising:
arranging a catheter comprising
an introduction unit with a top, said introduction unit also comprising a drainage lumen hole for drainage of a urinary bladder;
a balloon stopper unit in connection with and thus possible to fill via a balloon inflation connection and balloon filling tube arranged inside of the introduction unit, wherein filling of the balloon stopper unit with a fluid is intended when the balloon stopper unit is arranged inside of the bladder of a patient to provide for a stopper function of the balloon stopper unit against the bladder neck of the patient;
said catheter also comprising
an injection connection connected to an injection tube arranged inside of the introduction unit, which injection tube extends in a hollow tip arranged to be provided to extend from the introduction unit;
a drainage outlet;
inside of a urethra of a patient and anchored against the bladder neck of the patient subsequent to the filling of the balloon stopper unit with a fluid when the balloon stopper unit is arranged inside of the bladder of a patient; said method also comprising
injecting at least one anesthetic agent and adrenaline or injecting botulinum toxin (Botox) and/or penicillin to the prostate via the injection tube and the hollow tip at an intended position of the prostate.

According to this first general embodiment of the present invention, this involves arranging the catheter into the urethra and injecting at least one anesthetic agent and adrenaline or injecting botulinum toxin (Botox) and/or penicillin to the prostate via the injection tube and the hollow tip at an intended position of the prostate. First of all, the catheter in introduced into the urethra. The balloon stopper unit is filed with a fluid, suitably sterile water, so that the stopper unit starts working as an anchor holding the catheter in place. The drainage lumen hole is used for drainage of the urinary bladder.

Then, a movement back and forth is suggested to ensure that the catheter is securely positioned in the right place in the urethra. As hinted above, to simplify this, a lubricant, such as vaseline, may be used, or the introduction unit may have a sliding/slippery surface.

Finally, when the catheter is held in place, then the hollow tip is inserted into the prostate at the intended position. One important aspect according to the present invention is to ensure the correct locating of the hollow tip before inserting the same into the prostate. This is obtained by a suitable handling, and e.g. assisting means, such as a lubricant, and may also be accomplished by use of ultrasound or CT, and also by providing the hollow tip in a material simply to see when using such technology or by use nanoparticles inside the hollow tip so that these are visible after insertion into the prostate.

Furthermore, adrenaline is used to provide several actions. First of all, it is used to eliminate or at least diminish cooling down of the prostate during e.g. a heat treatment thereof. Secondly, adrenaline also ensures to suppress the blood supply to the prostate, which in turn is of interest to minimize the blood coming out at the surface of the prostate during a trimming action in a transurethral resection of the prostate (TURP) surgery. So, independently on the intended surgery used, adrenaline has an aided function. Adrenaline ensures less perioperative bleeding and total blood loss according to the present invention. Fact is that by injecting adrenaline before a TURP surgery, perioperative bleeding may be decreased substantially. The kit and method according to the present invention form the basis of injecting adrenaline at the right position(s) into the prostate before surgery thereof, which is yet a further improvement in relation to procedures used today. Moreover, a suitable anesthetic agent to be used together with adrenaline is carbocaine (mepivacaine). This is a preferred combination to be used according to the present invention.

Furthermore, the kit according to the present invention may also comprise other additives. One example is at least one cytostatic agent.

The catheter according to the present invention ensures the possibility of injecting at least one anesthetic agent and adrenaline or injecting botulinum toxin (Botox) and/or penicillin to the prostate via the injection tube and the hollow tip at an intended position of the prostate. Furthermore, as the injection tube and hollow tip is made in one piece and of a suitable (stiff but flexible) material, e.g. PEEK, this provides for the ability to remove the hollow tip from one site of the prostate to insert it at another site of the prostate in a subsequent step. This is described further below. Furthermore, in relation to the material of the injection tube, this should be stiff enough but still flexible, without deforming when being bended.

As mentioned above, there are different procedures used when treating prostates today. Both transurethral resection of the prostate (TURP) surgery and thermal treatments are being used frequently. The embodiments mentioned below are suitable to be used in such procedures. According to one embodiment of the present invention, the method involves injecting at least one anesthetic agent to the prostate via the hollow tip and injecting adrenaline to the prostate via the hollow tip during at least a first phase of the method, wherein at least the injecting of adrenaline to the prostate is performed sequentially. This embodiment implies using multiple injections of the adrenaline. This enables to trim part of the prostate into which part adrenaline has been injected, and then trim another part of the prostate after an additional injection of adrenaline into that part of the prostate. This further implies that the catheter being used is inserted and pulled out from the urethra before the trimming action and then inserted again when injecting a second dose of adrenaline, and so on. Both the anesthetic agent and adrenaline may be injected at the same time in these multiple injections.

With reference to a thermal treatment, the multiple injections of adrenaline and anesthetic agent is also of interest. Again, by decreasing the blood supply and cooling effect thereof, the thermal treatment effect is increased according to the present invention. It may be mentioned that this sequential mode may be obtained by using yet another catheter intended for the thermal treatment or may be obtained by including such functions (heating elements) in a catheter according to the present invention. Possible heating elements may operate based on different technologies, such as e.g. microwaves.

The procedure according to the present invention is beneficial as the effect of adrenaline decreases after injection into the prostate. The effect is kept at a high level during at least 10 minutes, and up to 15 minutes, but then decreases. Therefore, it is beneficial to inject adrenaline into one volume and then trim this part and then inject adrenaline again at another part and then trim that part. As such, the bleeding may be suppressed, which is beneficial when performing trimming of or heat treatment to the prostate. In relation to a heat treatment it is beneficial to anesthetize the entire prostate as the heat treatment is performed on a large part of the surface, said heat treatment being evenly distributed extending out from the urethra.

Furthermore, with reference to changing the injection position of the prostate, according to one embodiment of the present invention, the method involves changing the position of the hollow tip in the prostate to enable for at least injection of adrenaline at different positions in the prostate, preferably for injection of at least one anesthetic agent, such as carbocaine, and adrenaline at different positions in the prostate. Suitably, adrenaline and carbocaine is admixed in the syringes being used.

According to yet another embodiment of the present invention, linked to a TURP treatment, the method involves injecting both at least one anesthetic agent and adrenaline to one first half of the prostate, then removing the catheter from the patient and performing trimming of that first half of the prostate in a transurethral resection of the prostate surgical treatment, then inserting the catheter again into the patient and injecting both at least one anesthetic agent and adrenaline to the second half of the prostate, then removing the catheter from the patient again and performing trimming of that second half of the prostate.

As an example, first a left side of the prostate in injected with a mixture of adrenaline and carbocaine. Then the catheter is removed from the urethra and trimming is performed on the left side of the prostate. The blood supply is diminished by use of the adrenaline and carbocaine so that the TURP trimming is possible to perform with strong visibility and in a safe way. Then the catheter is inserted again, and injection is performed on the right side of the prostate. The catheter is removed again, and trimming is performed on the right side of the prostate.

In relation to performing a thermal treatment of a prostate, according to one embodiment of the present invention, the method involves injecting both at least one anesthetic agent and adrenaline to one part of the prostate, then supplying heat to the surface of the prostate at a corresponding position to that part of the prostate, then injecting both at least one anesthetic agent and adrenaline to another part of the prostate and then supplying heat to the surface of the prostate at a corresponding position to that other part of the prostate, optionally by removing the catheter from the patient after the injecting of at least one anesthetic agent and adrenaline and inserting another catheter for enabling the supplying of heat via one or more heating elements. According to this embodiment, another catheter is used for enabling the supplying of heat via one or more heating elements. According to the present invention, the catheter according to the present invention may include such functionality, i.e. also having heating elements intended for supplying heat to a prostate surface.

As mentioned above, the time frames used are relevant with reference to the effect of adrenaline. As a consequence, according to one embodiment of the present invention, the method involves a sequence of injecting both at least one anesthetic agent and adrenaline to a volume of the prostate and then performing trimming in a transurethral resection of the prostate (TURP) surgical treatment or a heat treatment of a corresponding surface of the prostate within a time frame of maximum 25 minutes, preferably maximum 20 minutes, more preferably maximum 15 minutes, and then performing yet another similar sequence to another volume of the prostate.

Moreover, as hinted above, the prostate may be divided into different sections to ensure an efficient and safe treatment. Therefore, according to one embodiment of the present invention, the method involves injecting at least adrenaline, preferably both at least one anesthetic agent, such as carbocaine, and adrenaline, sequentially to different parts of the prostate, preferably to at least two different positions of the prostate, more preferably to four different squares of the prostate.

Furthermore, also locating the hollow tip to ensure an intended position for the injection into the prostate is of relevance according to the present invention. Therefore, according to one embodiment of the present invention, the method involves means for locating the hollow tip. According to one specific embodiment, said means for locating is an external means, preferably an ultrasound device or a CT (computed tomography) device, or internal means to be injected through the hollow tip, preferably nanoparticles. As an example, robotic CT technology may be used, such as together with a robotic arm.

Moreover, as mentioned above, also a lubricant, such as vaseline, may be used to ensure that the catheter is simple to pull back and forth inside of the urethra, both to find the right position and also to simplify for removal and insertion of a catheter according to the present invention. Therefore, also the use of a lubricant may be seen as means to increase the correct locating of the catheter and hollow tip before inserting/introducing the hollow tip into the prostate.

Furthermore, the method according to the present invention may also involve using complementing additives. In line with this, according to one embodiment of the present invention, the method also involves injecting one or more cytostatic agents to the prostate. Cytostatic agents may as such be used as an aid for the treatment of prostate cancer.

Moreover, the method according to the present invention may also be used in combination with the injection of botulinum toxin (Botox) and/or penicillin. Therefore, according to one embodiment of the present invention, the method involves injecting botulinum toxin (Botox) and/or penicillin to the prostate, preferably injecting botulinum toxin (Botox) and/or penicillin to a lower part of the prostate. According to one embodiment, injecting botulinum toxin (Botox) and/or penicillin to the prostate is performed as a treatment of prostatitis. Botox is then used according to the present invention to kill nerves in the prostate, and as a treatment of prostatitis. Penicillin may also be used as a treatment or prevention of prostatitis.

It should also be noted that the kit according to the present invention may include a separate syringe containing botulinum toxin (Botox) and/or penicillin.

Furthermore, the kit also comprises at least one or more syringe(s) 1000 connectable to the injection connection 8 of the catheter 1 and containing adrenaline and at least one anesthetic agent, and/or at least a syringe 1000 or vial containing botulinum toxin (Botox) and/or penicillin.

Figure 1:
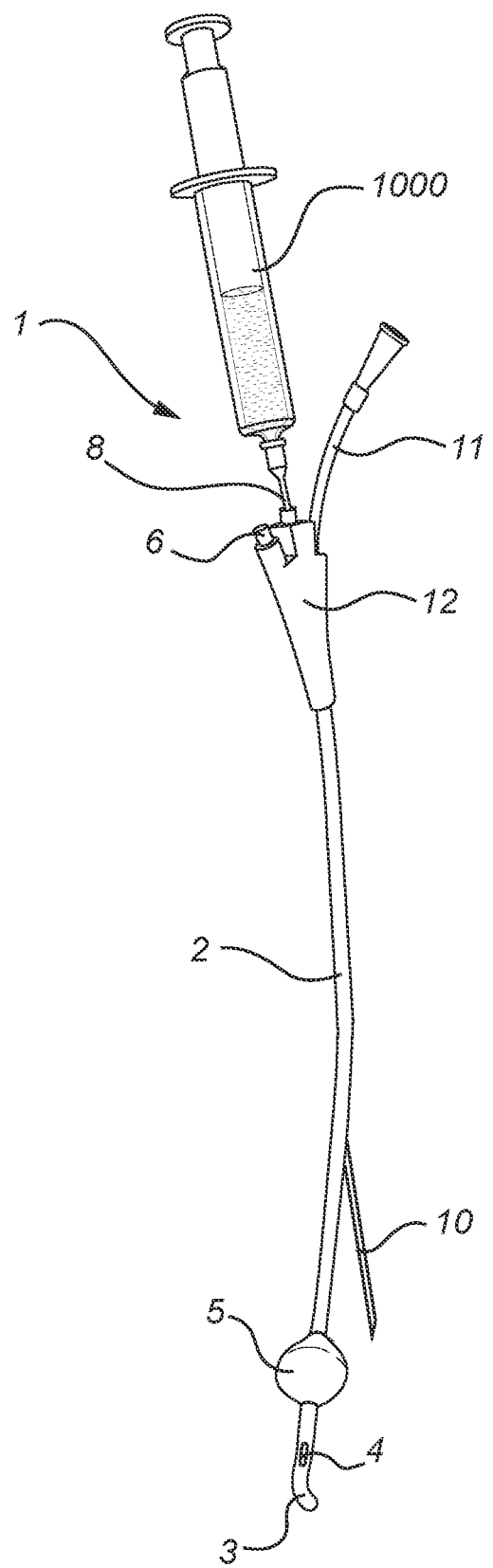
In FIG. 1 there is disclosed a kit according to one embodiment of the present invention. The kit comprises a catheter 1 comprising an introduction unit 2 with a top 3, said introduction unit 2 also comprising a drainage lumen hole 4 for drainage of a urinary bladder. Moreover, the catheter 1 also comprises a balloon stopper unit 5 in connection with and thus possible to fill via a balloon inflation connection 6 and balloon filling tube arranged inside of the introduction unit 2. The filling of the balloon stopper unit 5 with a fluid is intended when the balloon stopper unit 5 is arranged inside of the bladder of a patient to provide for a stopper function of the balloon stopper unit 5 against the bladder neck of the patient. The catheter 1 also comprises an injection connection 8 connected to an injection tube 9 arranged inside of the introduction unit 2, which injection tube 9 extends in a hollow tip 10 arranged to be provided to extend from the introduction unit 2 and into the prostate of a patient. The catheter 1 also comprises a drainage outlet 11. Moreover, according to this embodiment, the catheter 1 has a multi-connection unit 12 which holds the balloon inflation connection 6, the injection connection 8 and at least a first portion of the drainage outlet 11.
Figure 2:
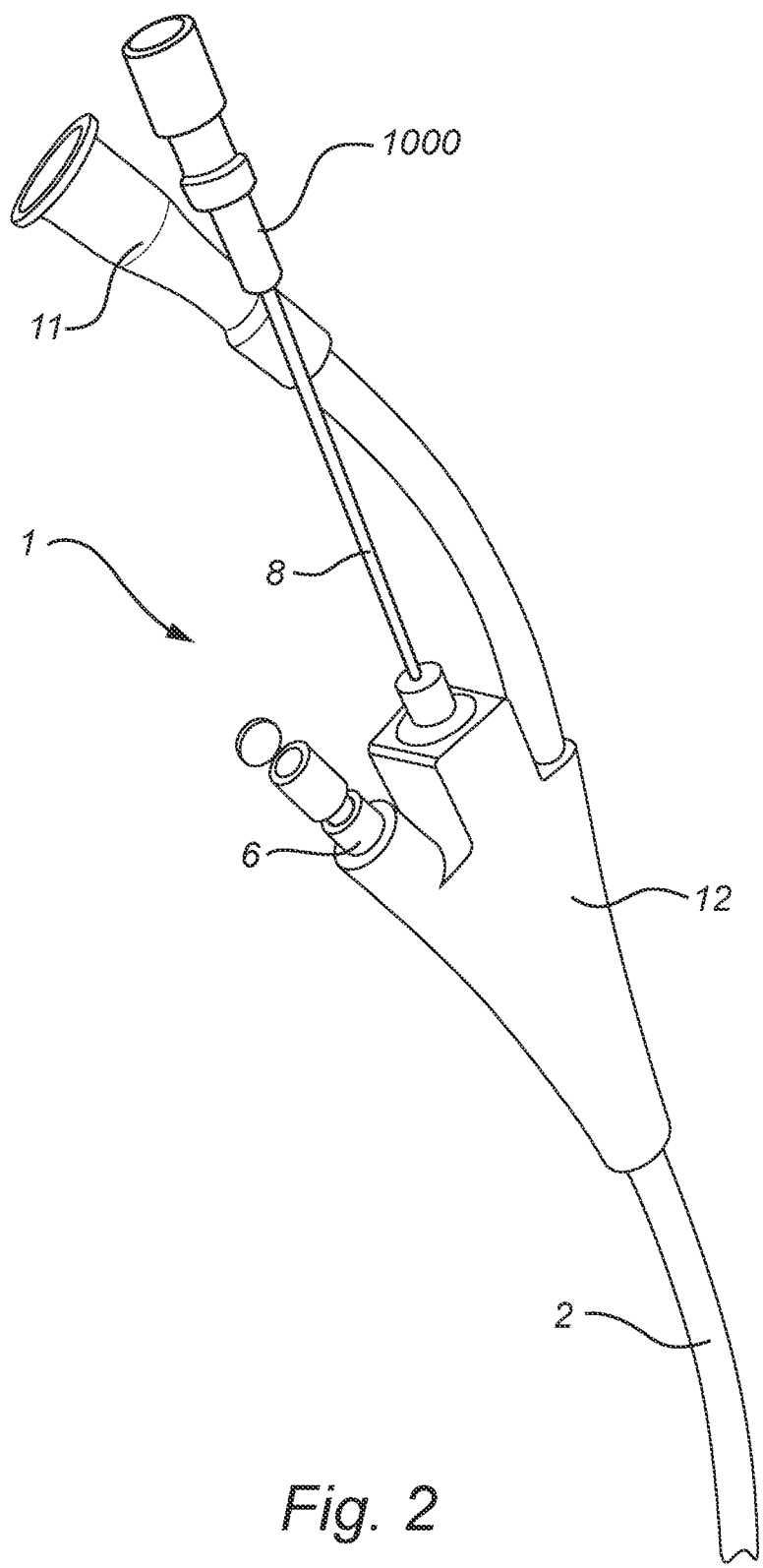

In FIG. 2 there is disclosed a part shown of the catheter 1 according to the embodiment of a kit according to the embodiment shown in FIG. 1.

The invention claimed is:

1. A method for performing a prostate surgical treatment, said method comprising:
    arranging a catheter comprising:
        an introduction unit with a top, said introduction unit also comprising a drainage lumen hole for drainage of a urinary bladder;
        a balloon stopper unit in connection with and thus possible to fill via a balloon inflation connection and balloon filling tube arranged inside of the introduction unit, wherein filling of the balloon stopper unit with a fluid is intended when the balloon stopper unit is arranged inside of the bladder of a patient to provide for a stopper function of the balloon stopper unit against a bladder neck of the patient;
        an injection connection connected to an injection tube arranged inside of the introduction unit, which injection tube extends in a hollow tip arranged to be provided to extend from the introduction unit; and
        a drainage outlet;
    inside of a urethra of a patient and anchored against the bladder neck of the patient subsequent to the filling of the balloon stopper unit with the fluid when the balloon stopper unit is arranged inside of the bladder of a patient,
    injecting at least one anesthetic agent and adrenaline to the prostate via the injection tube and the hollow tip at an intended position of the prostate; and
    changing the position of the hollow tip in the prostate to enable at least injection of said at least one anesthetic agent at different positions in the prostate; and
    injecting both at least one anesthetic agent and adrenaline to one first half of the prostate, then removing the catheter from the patient and performing trimming of that first half of the prostate in a transurethral resection of the prostate (TURP) surgical treatment, then inserting the catheter again into the patient and injecting both at least one anesthetic agent and adrenaline to a second half of the prostate, then removing the catheter from the patient again and performing trimming of that second half of the prostate.

2. The method according to claim 1, further comprising injecting at least one anesthetic agent to the prostate via the hollow tip and injecting adrenaline to the prostate via the hollow tip during at least a first phase of the method, wherein at least the injecting of adrenaline to the prostate is performed sequentially.

3. The method according to claim 2, further comprising injecting both at least one anesthetic agent and adrenaline, sequentially to different parts of the prostate.

4. The method according to claim 3, further comprising injecting both at least one anesthetic agent and adrenaline sequentially to at least four different squares of the prostate.

5. The method according to claim 1, further comprising changing the position of the hollow tip in the prostate to enable injection of at least one anesthetic agent and adrenaline at different positions in the prostate.

6. The method according to claim 1, further comprising injecting both at least one anesthetic agent and adrenaline to one part of the prostate, then supplying heat to the surface of the prostate at a corresponding position to that part of the prostate, then injecting both at least one anesthetic agent and adrenaline to another part of the prostate and then supplying heat to the surface of the prostate at a corresponding position to that other part of the prostate.

7. The method according to claim 2, further comprising a sequence of injecting both at least one anesthetic agent and adrenaline to a volume of the prostate and then performing trimming in a transurethral resection of the prostate (TURP) surgical treatment or a heat treatment of a corresponding surface of the prostate within a time frame of maximum 25 minutes, and then performing yet another similar sequence to another volume of the prostate.

8. The method according to claim 1, wherein the method involves means for locating the hollow tip.

9. The method according to claim 8, wherein said means for locating is an external means.

10. The method according to claim 1, further comprising injecting one or more cytostatic agents to the prostate.

11. The method according to claim 1, further comprising injecting at least one of botulinum toxin (Botox) or at least one antibiotic agent to the prostate.

12. The method according to claim 11, wherein injecting at least one of botulinum toxin (Botox) or at least one antibiotic agent to the prostate is performed as a treatment of prostatitis.

13. The method according to claim 11, wherein said at least one antibiotic agent is penicillin.

* * * * *